United States Patent
Namiki

(10) Patent No.: US 9,585,724 B2
(45) Date of Patent: Mar. 7, 2017

(54) SURGICAL SYSTEM

(75) Inventor: Hirotaka Namiki, Tokorozawa (JP)

(73) Assignee: OLYMPUS CORPORATION, Tokyo (JP)

( * ) Notice: Subject to any disclaimer, the term of this patent is extended or adjusted under 35 U.S.C. 154(b) by 846 days.

(21) Appl. No.: 13/418,683

(22) Filed: Mar. 13, 2012

(65) Prior Publication Data

US 2012/0239058 A1 Sep. 20, 2012

(30) Foreign Application Priority Data

Mar. 15, 2011 (JP) ................................ 2011-057050

(51) Int. Cl.
*G06K 9/00* (2006.01)
*A61B 1/04* (2006.01)
*A61B 17/00* (2006.01)

(52) U.S. Cl.
CPC .............. *A61B 34/30* (2016.02); *A61B 34/37* (2016.02); *A61B 1/04* (2013.01); *A61B 2017/00119* (2013.01); *A61B 2090/373* (2016.02)

(58) Field of Classification Search
CPC A61B 2017/00119; A61B 2017/00123; A61B 19/2203; A61B 19/2223; A61B 2019/5225; A61B 2019/5231; A61B 19/5244; A61B 2019/2211; A61B 1/04
See application file for complete search history.

(56) References Cited

U.S. PATENT DOCUMENTS

| | | | |
|---|---|---|---|
| 9,218,053 B2* | 12/2015 | Komuro | A61B 18/1402 |
| 2008/0242929 A1 | 10/2008 | Ito | |
| 2009/0074269 A1* | 3/2009 | Nishimura et al. | 382/128 |
| 2011/0279268 A1* | 11/2011 | Konishi | A61B 17/32006 340/540 |

FOREIGN PATENT DOCUMENTS

| | | |
|---|---|---|
| EP | 0 734 742 A2 | 10/1996 |
| EP | 1 103 223 A2 | 5/2001 |
| EP | 1 974 652 A1 | 10/2008 |
| JP | 9-066056 | 3/1997 |
| JP | 09-066056 | 3/1997 |

(Continued)

OTHER PUBLICATIONS

Karkanis et al., "Tumor recognition in endoscopic video images using artificial neural network architectures", Sep. 7, 2000, IEEE, Proc. of the 26th Euromicro Conference, vol. 2, p. 423-429.*

(Continued)

*Primary Examiner* — Chan Park
*Assistant Examiner* — Timothy Choi
(74) *Attorney, Agent, or Firm* — Scully, Scott, Murphy & Presser, PC

(57) ABSTRACT

According to one embodiment, a surgical system includes an imaging system, a determination unit, and a control unit. The imaging system is configured to acquire image information. The determination unit is configured to determine, based on the image information, whether an abnormal state has occurred in the surgical system. The control unit is configured to switch to an abnormality time control mode of executing abnormality-handling processing, when the determination unit determines that an abnormal state has occurred.

4 Claims, 5 Drawing Sheets

(56) References Cited

FOREIGN PATENT DOCUMENTS

| | | |
|---|---|---|
| JP | 2003-334164 A | 11/2003 |
| JP | 3717552 | 9/2005 |
| JP | 2005-296198 A | 10/2005 |
| JP | 2006-25912 A | 2/2006 |
| JP | 2007-7040 A | 1/2007 |
| JP | 2008-194179 | 8/2008 |
| JP | 2008-237395 | 10/2008 |
| JP | 2009-225851 A | 10/2009 |
| JP | 2010-004979 | 1/2010 |
| JP | 2010-51633 A | 3/2010 |
| WO | 2006/091494 A1 | 8/2006 |

OTHER PUBLICATIONS

Kazuhisa et al., "Machine Translation of JP 2009-225851", Oct. 8, 2009, Espacenet, p. 1-51.*
Extended Supplementary European Search Report dated Sep. 8, 2014 from related European Application No. 12 757 164.4.
English translation of International Search Report PCT/JP2012/056261 dated Apr. 3, 2012.
English Abstract of Japanese Patent Publication No. 9-066056, dated Mar. 11, 1997.
Japanese Office Action dated Feb. 17, 2015 from Japanese Patent Application No. 2011-057050, together with an English language translation.
Chinese Office Action dated Sep. 29, 2015 from related Chinese Patent Application No. 201280012794.2, together with an English language translation.

* cited by examiner

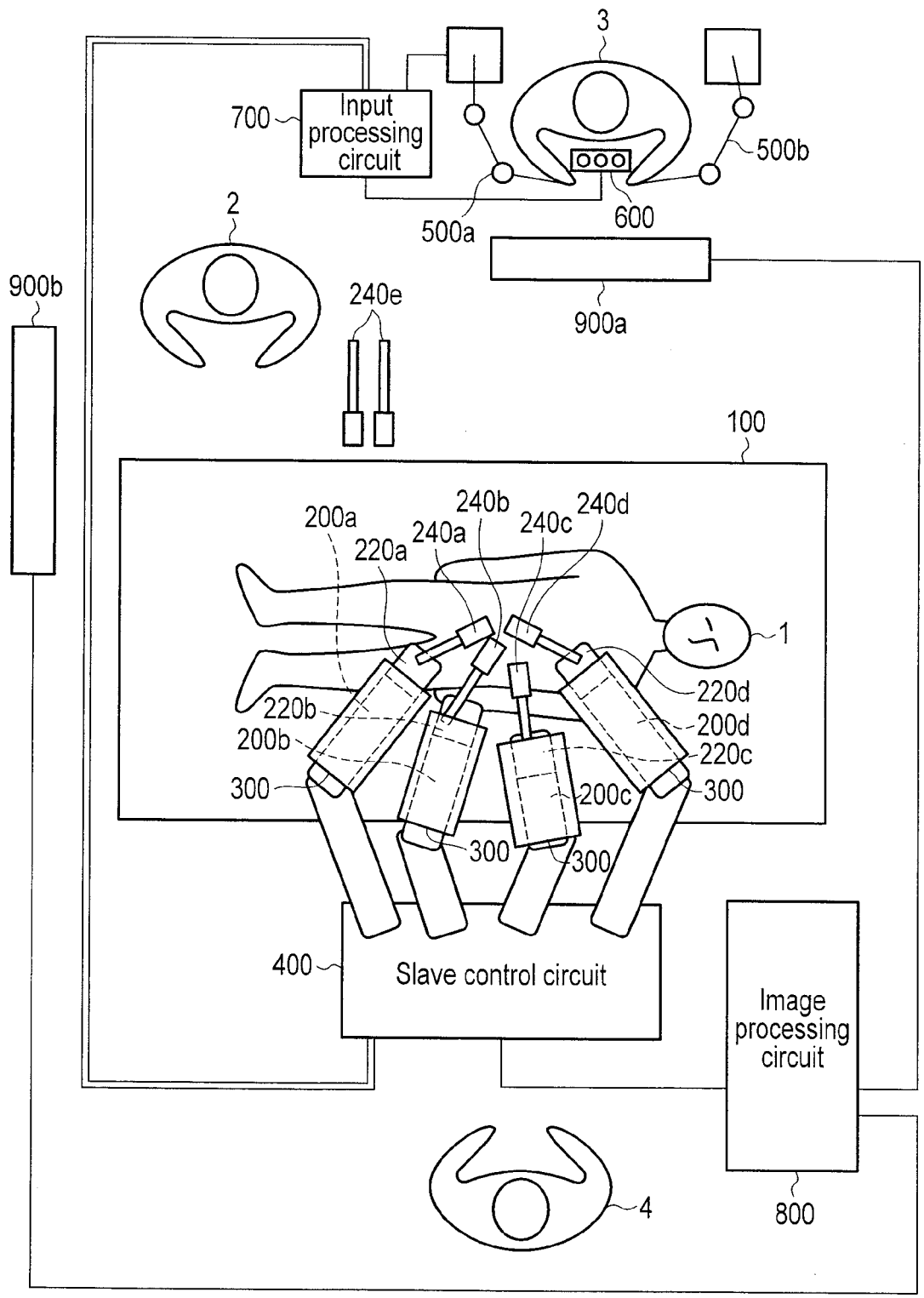
F I G. 1

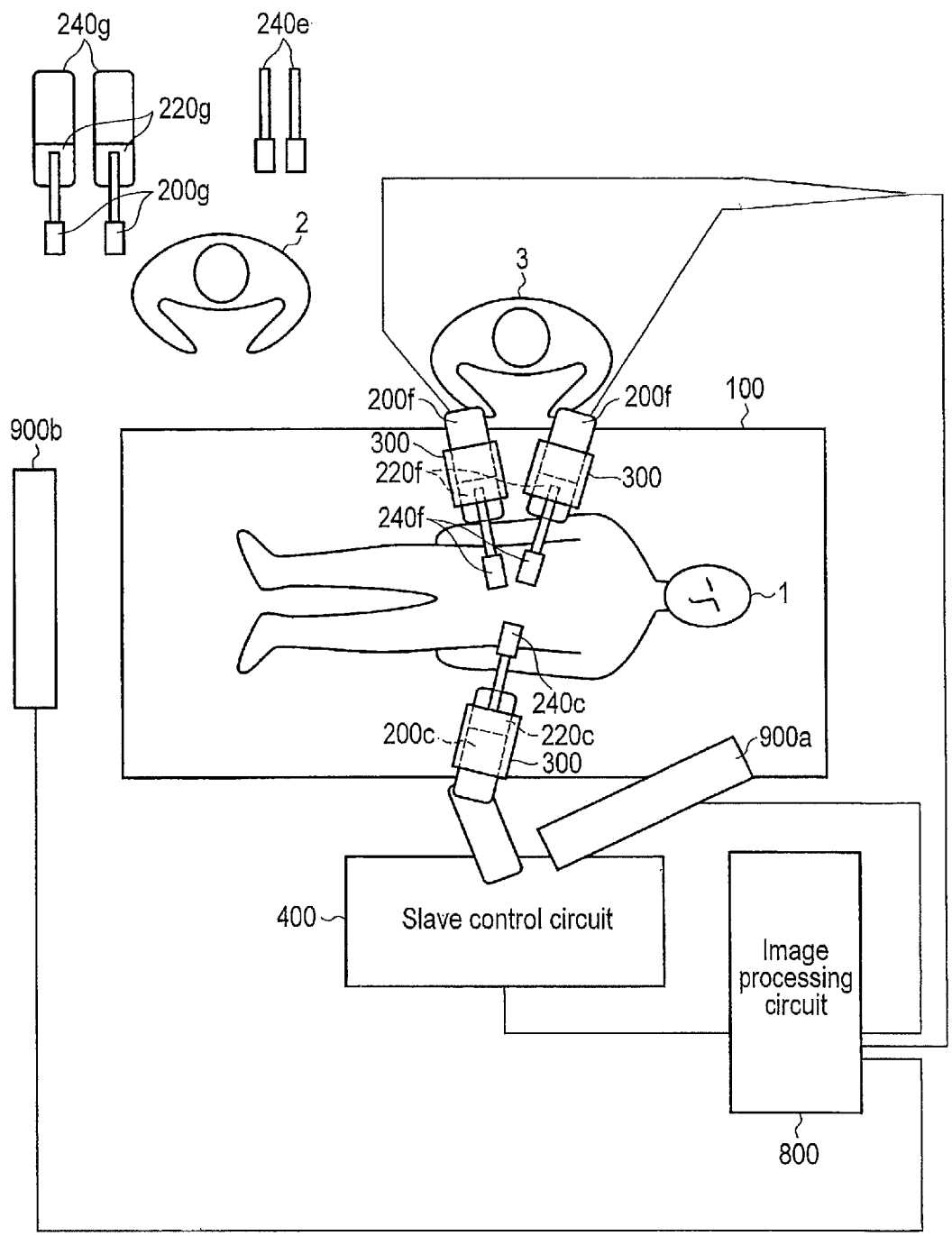
F I G. 2

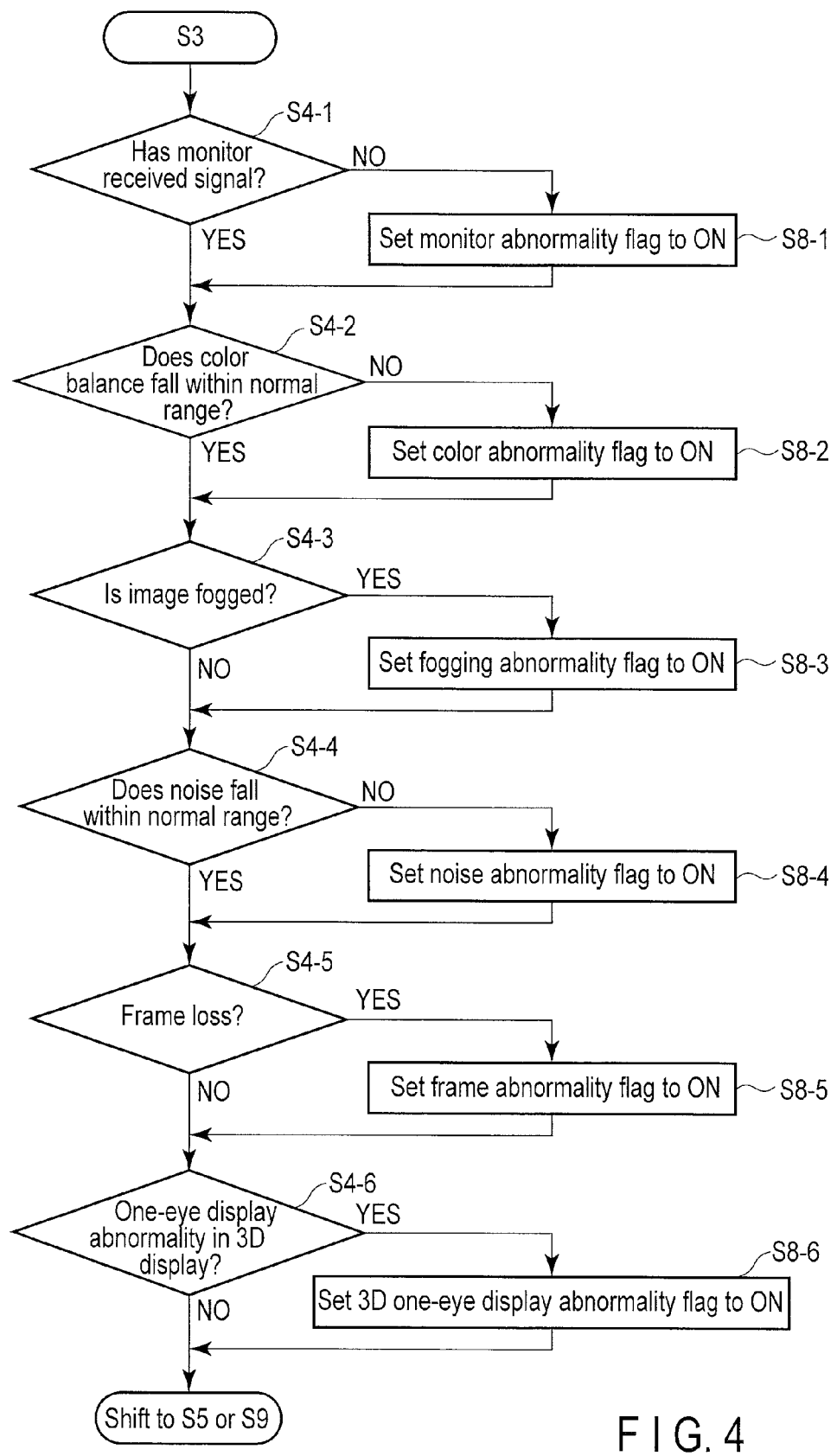
F I G. 4

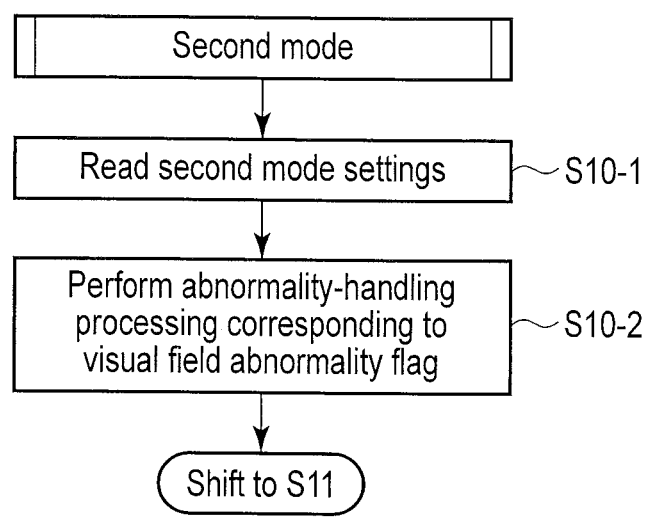
F I G. 5

/ 1

SURGICAL SYSTEM

CROSS-REFERENCE TO RELATED APPLICATIONS

This application is based upon and claims the benefit of priority from prior Japanese Patent Application No. 2011-057050, filed Mar. 15, 2011, the entire contents of which are incorporated herein by reference.

BACKGROUND OF THE INVENTION

1. Field of the Invention

The present invention relates to a surgical system such as a medical manipulator system.

2. Description of the Related Art

Recently, there have been proposed various types of techniques associated with medical treatments using robots. In the field of surgery, in particular, various types of medical manipulator systems have been proposed, which treat patients by using multi-degree-of-freedom manipulators having multi-degree-of-freedom arms.

For example, Japanese Patent No. 3717552 discloses a medical manipulator system excellent in safety and operability, which can quickly handle operation errors in a plurality of medical manipulators in surgeries using the manipulators.

More specifically, in the medical manipulator system disclosed in Japanese Patent No. 3717552, when an infrared sensor detects a predetermined amount of infrared light, a sensor processing circuit recognizes it, and the operation of a slave manipulator for treatment is stopped.

If, for example, the sensor processing circuit determines that the detection data value from the infrared sensor is equal to or more than a preset threshold, the sensor processing circuit sends a stop instruction to a servo processing circuit which actually controls the slave manipulator for treatment, thereby stopping the operation of the slave manipulator for treatment. This can prevent the distal end of the treatment tool from unintentionally coming into contact with an organ.

BRIEF SUMMARY OF THE INVENTION

In order to achieve the above object, according to an aspect of the present invention, there is provided a surgical system including an imaging system configured to acquire image information, the system comprising:

a determination unit configured to determine, based on the image information, whether an abnormal state has occurred in the surgical system; and a control unit configured to switch to an abnormality time control mode of executing abnormality-handling processing, when the determination unit determines that an abnormal state has occurred.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing the first arrangement example of a surgical system according to an embodiment of the present invention;

FIG. 2 is a view showing the second arrangement example of the surgical system according to the surgical system according to the embodiment of the present invention;

FIG. 4 is a flowchart showing the details of processing in step S4 in the flowchart shown in FIG. 3 (branching from step S4 to step S5 or step S8; the processing in a region D surrounded by the broken line in the flowchart of FIG. 3); and FIG. 5 is a flowchart showing a subroutine for processing (setting processing for the second mode) in step S10 in the flowchart shown in FIG. 3.

DETAILED DESCRIPTION OF THE INVENTION

Figure 3:
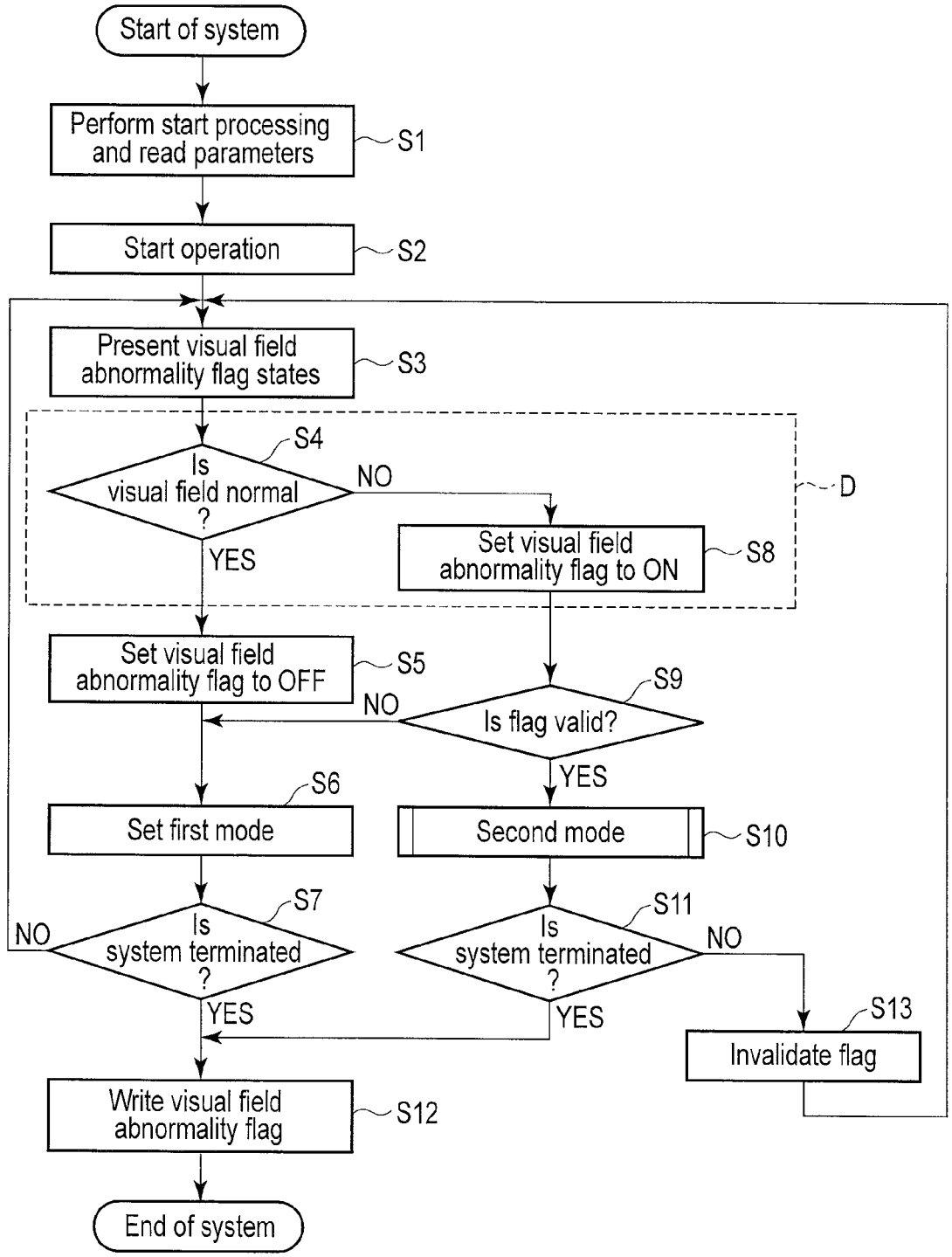
FIG. 3 is a flowchart showing an example of the processing of handling an abnormal state which has occurred in the surgical system according to the embodiment of the present invention.

An embodiment of the present invention will be described below with reference to the views of the accompanying drawing.

FIG. 1 is a view showing the first arrangement example of a surgical system according to the embodiment. This example is premised on a surgical system based on a master-slave scheme. In this case, the surgical system based on the master-slave scheme includes two kinds of arms including master arms and slave arms and a system which remotely controls the slave arms so as to follow up the operation of the master arms.

The surgical system shown in FIG. 1 includes an operating table 100, slave arms 200a to 200d, a slave control circuit 400, master arms 500a and 500b, an operation unit 600, an input processing circuit 700, an image processing circuit 800, and displays 900a and 900b.

The operating table 100 is a table on which a patient 1 to be observed and treated is placed. The plurality of slave arms 200a, 200b, 200c, and 200d are installed near the operating table 100. Note that the slave arms 200a to 200d may be installed on the operating table 100.

The slave arms 200a, 200b, 200c, and 200d respectively have a plurality of multi-degree-of-freedom joints. The slave arms 200a, 200b, 200c, and 200d position various kinds of tools such as treatment tools and observation tools attached to the distal end sides of the slave arms 200a to 200d (the sides facing the body cavity of the patient 1) with respect to the patient 1 placed on the operating table 100 by bending the respective joints.

The joints of the slave arms 200a to 200d are independently driven by the power units provided in the respective arms. As such power unit, for example, a motor (servo motor) is used, which has a servo mechanism including an incremental encoder and a reduction gear. The slave control circuit 400 controls the operation of this servo motor.

The slave arms 200a to 200d also include a plurality of power units for driving tools 240a to 240d attached to the respective distal end sides. As such power unit, for example, a servo motor is also used. The slave control circuit 400 also controls the operation of this servo motor.

When the power units of the slave arms 200a to 200d are driven, position detectors detect the driving amounts of the motors. The slave control circuit 400 receives detection signals from the position detectors, and detects the driving amounts of the slave arms 200a to 200d based on the detection signals.

Surgical power transmission adapters (to be simply referred to as adapters hereinafter) 220a, 220b, 220c, and 220d are respectively interposed between the slave arms 200a, 200b, 200c, and 200d and the tools 240a, 240b, 240c, and 240d to respectively connect the slave arms 200a, 200b, 200c, and 200d to the tools 240a, 240b, 240c, and 240d. Although described in detail later, the adapters 220a to 220d respectively have linear-driving mechanisms and are configured to transmit the powers generated by the power units of the corresponding slave arms to the corresponding tools by linear-driving motion.

The tools 240a to 240d respectively have multi-degree-of-freedom joint portions and are inserted into the body cavity of the patient 1 through an insertion hole (not shown) formed in the body wall of the patient 1. The distal end portions of the tools 240a to 240d are configured to be driven to bend and rotate.

This bending driving operation is performed by, for example, driving the servo motors respectively provided in the slave arms 200a to 200d so as to push and pull wires extending through the tools 240a to 240d. This rotating driving operation is performed by, for example, driving the servo motors respectively provided in the slave arms 200a to 200d so as to actuate the rotating mechanisms respectively provided in the tools 240a to 240d.

In addition, some type of tool has an opening/closing mechanism at its distal end. This opening/closing mechanism is, for example, a mechanism for the operation of gripping a tool such as a needle or a thread for treatment, the blood vessel, the organ, the fat, or the like. Such opening/closing mechanisms are also actuated by, for example, driving the servo motors respectively provided in the slave arms 200a to 200d so as to push and pull the wires extending through the tools.

Of the four slave arms 200a to 200d shown in FIG. 1, for example, the slave arms 200a, 200b, and 200d are used as slave arms for treatment. Various kinds of surgical tools are attached as the tools 240a, 240b, and 240d to the slave arms 200a, 200b, and 200d for treatment.

Assume that surgical tools in this embodiment include, for example, tools to treat tissue regions in the body of the patient 1, e.g., a scalpel and scissors. The slave arm 200c is used as a camera arm for observation. Various kinds of observation tools, each serving as the tool 240c, are attached to the slave arm 200c. Assume that observation tools in the embodiment include tools for the observation of tissue regions in the body of the patient 1, e.g., an electronic endoscope.

The tools 240a to 240d attached to the adapters 220a to 220d can be replaced with replacement tools 240e. For example, an assistant 2 performs replacing operation for such tools.

A drape 300 is used to separate a portion to be sterilized (to be referred to as a clean area hereinafter) from a portion not to be sterilized (to be referred to as an unclean area hereinafter) in the surgical system according to this embodiment.

For example, surgical tools such as a scalpel and scissors come into direct contact with the inside of the body cavity of the patient 1, and hence need to be sufficiently cleaned and sterilized in advance. In contrast, the power units and the like of the slave arms 200a to 200d include various kinds of electronic components, and hence are not generally structured to withstand sterilization processing.

When performing surgery while the tools 240a to 240d are attached to the slave arms 200a to 200d through the adapters 220a to 220d, the operator performs surgery while the drapes 300 cover the portions of the slave arms 200a to 200d which correspond to the power units so as to expose the portions corresponding to the tools 240a to 240d and protect the power units of the slave arms 200a to 200d, as shown in FIG. 1.

Separating the clean areas from the unclean areas by using the drapes 300 will prevent confusion between the clean and unclean areas during surgery.

The slave control circuit 400 includes, for example, a CPU and a memory. The slave control circuit 400 stores predetermined programs for controlling the slave arms 200a to 200d, and controls the operations of the slave arms 200a to 200d or the tools 240a to 240d in accordance with control signals from the input processing circuit 700.

That is, based on control signals from the input processing circuit 700, the slave control circuit 400 specifies a slave arm (or a tool) as an operation target of a master arm operated by an operator 3 and computes a driving amount necessary to move the specified slave arm (tool) in accordance with the operation amount of the master arm by the operator 3. The slave control circuit 400 then controls the operation of the slave arm as the operation target of the master arm in accordance with the calculated driving amount. At this time, the slave control circuit 400 inputs a driving signal to the corresponding slave arm and controls the magnitude and polarity of a driving signal to set the driving amount of the slave arm as the operation target to a target driving amount in accordance with a detection signal input from the position detector of the power unit in accordance with the operation of the corresponding slave arm.

In addition, upon receiving an image signal from the observation tool attached to the slave arm 200c, the slave control circuit 400 outputs the input image signal to the image processing circuit 800. Although described in detail later, the image processing circuit 800 detects (determines) a visual field abnormality based on this image signal. The image processing circuit 800 switches control modes (first and second modes) based on this visual field abnormality detection (determination) result. In this case, the slave control circuit 400 controls the operation of each slave arm so as to execute processing in each control mode based on a control signal from the image processing circuit 800.

As shown in FIG. 1, an ME 4 as an engineer who checks the state and the like of the surgical system according to this embodiment is sometimes located near the slave control circuit 400.

The control modes (first and second modes) will be described in detail below.

The "first mode" is the control mode to be set at normal state (when no abnormality has occurred in the imaging system). In contrast, the "second mode" is the control mode to be set when the image acquired by the imaging system is not properly displayed (abnormal state). The second mode is the control mode in which the content of an abnormal state (an "abnormal detection pattern" to be described later) which has occurred is associated with the content of processing to be executed at the occurrence of an abnormality ("abnormality-handling processing" to be described later).

Association setting in the second mode is properly performed in accordance with, for example, the contents of an abnormal state and/or the operator of this surgical system. This setting may be defined in advance or may be changed by the operator as needed.

The contents of an abnormality (abnormality detection pattern) are, for example, the contents of an abnormality corresponding to each abnormality flag (to be described later).

<<Abnormality Detection Pattern 1>> Monitor Abnormality

The displays 900a and 900b have received no image data (the monitors have received no signals).

<<Abnormality Detection Pattern 2>> Color Abnormality

The colors of a displayed image are inadequate (the RGB balance is extremely poor).

<<Abnormality Detection Pattern 3>> Fogging Abnormality

The lens of the slave arm 200c which is a camera arm for observation is fogged and has decreased in brightness, resulting in an edgeless image.

<<Abnormality Detection Pattern 4>> Noise Abnormality

An image signal is mixed with noise originating from the power supply system (a large peak appears at a specific frequency upon frequency analysis of an image signal).

<<Abnormality Detection Pattern 5>> Frame Abnormality

A frame loss has occurred (a timeout has been detected because image processing cannot catch up with display update processing).

<<Abnormality Detection Pattern 6>> One-Eye Display Abnormality in 3D Display

One-eye display is performed in the 3D display mode (images from two endoscopes (left and right endoscopes) for acquiring 3D display images greatly differ from each other).

Obviously, <<abnormality detection patterns>> described above are merely examples, and abnormality detection patterns to which the present invention is to be applied are not limited to them.

Of the above abnormality detection patterns, <<abnormality detection pattern 1>> and <<abnormality detection pattern 6>> are abnormal states originating from abnormalities in the imaging system, and <<abnormality detection pattern 2>> to <<abnormality detection pattern 5>> are abnormal states associated with displayed images.

For example, the following types of processing are the contents of processing (abnormality-handling processing) to be executed at the occurrence of the above abnormalities.

<<Abnormality-Handling Processing 1>> Stop Processing on Site

At least one of the slave arms 200a to 200d is stopped onsite.

<<Abnormality-Handling Processing 2>> Stop Processing Upon Withdrawal

At least one of the slave arms 200a to 200d is stopped upon withdrawal from the body of the patient 1.

<<Abnormality-Handling Processing 3>> Stop Processing Upon Withdrawal after Releasing the Held State by the Tool After the operator releases the held state by at least one of the tools (surgical tools) 240a, 240b, and 240d of the slave arms 200a, 200b, and 200d, at least one of the slave arms 200a, 200b, and 200d is stopped upon withdrawal from the body of the patient 1.

<<Abnormality-Handling Processing 4>> Stop Processing Upon Withdrawal of Arm for Tool after Wide Visual Field is Secured by Withdrawal of Arm for Imaging System The system withdraws the slave arm 200c (e.g., an endoscope) to which an observation tool is attached as the tool 240c to secure a wide visual field with the endoscope, and stops at least one of the slave arms 200a, 200b, and 200d to which the tools (surgical tools) 240a, 240b, and 240d are attached upon withdrawal from the body of the patient 1.

<<Abnormality-Handling Processing 5>> Processing of Presenting Operator, Assistant, ME, and Like with Possibility of Abnormality in Image (Alarming or Warning)

The system informs the operator 3 and/or the assistant 2 by sound, video, or the like that abnormalities may have occurred in the images reproduced and displayed on the displays 900a and 900b.

<<Abnormality-Handling Processing 6>> Processing of Presenting Operator, Assistant, ME, or Like with Contents of Abnormality (Display Abnormality, Color Misregistration, Fogging, One-Eye Display, or Like) when Abnormality May have Occurred in Image If abnormalities may have occurred in the images reproduced and displayed on the displays 900a and 900b, the system informs the operator 3 and/or the assistant 2 of the contents of the abnormalities by sound, video, or the like.

<<Abnormality-Handling Processing 7>> No Special Processing

Even if an abnormality has occurred in the imaging system, special processing is not always required. If, therefore, there is no need to perform special processing, the system performs no special processing (this state is substantially the same as the state in which the system is set in the "first mode" which is the processing mode at normal state (when no abnormality has occurred in the imaging system)).

Obviously, each <<abnormality-handling processing>> described above is merely an example, and the present invention is not limited to each example described above.

In the "second mode", each <<abnormality detection pattern>> is associated with corresponding <<abnormality-handling processing>>, and each combination of <<abnormality detection pattern>> and <<abnormality-handling processing>> may be defined in advance or may be arbitrarily set by the user.

In addition, in the "second mode", for example, the following setting may be performed.

[Setting to Assign Priority Levels to Visual Field Abnormality Flags]

To handle a case in which a plurality of visual field abnormality flags are simultaneously set to ON, priority levels are assigned to the respective abnormality flags. If a plurality of visual field abnormality flags are set to ON, the system executes abnormality-handling processing corresponding to a visual field abnormality flag with a higher priority level.

[Setting to Change Abnormality-Handling Processing Based on Number of Times Abnormality Flag is Set to ON]

For example, when a given visual field abnormality flag is set to ON for the first time, the system executes <<abnormality-handling processing 5>>. When this flag is set to ON for the second time, the system executes <<abnormality-handling processing 6>>.

[Setting to Assign Weight to Each Abnormality Detection Pattern]

Assume that a weight has been assigned to each abnormality detection pattern, and the sum of weights corresponding to abnormalities which have occurred has reached a predetermined value. In this case, the system changes <<abnormality-handling processing>>.

The setting of the "second mode" has been described above. This setting may be predetermined setting or may be arbitrarily made by the user. In addition, it is possible to change the setting, as needed, in accordance with the surgical experience and skill level of the operator of this surgical system, a surgical target region, and the like.

The master arms 500a and 500b are formed by a plurality of link mechanisms. Each link forming a link mechanism is provided with, for example, a position detector such as an incremental encoder. Detecting the operation of each link using this position detector allows the input processing circuit 700 to detect the operation amounts of the master arms 500*a* and 500*b*.

In the example shown in FIG. 1, the operator 3 operates the master arm 500*a* with his/her right hand, and operates the master arm 500*b* with his/her left hand. FIG. 1 shows a case in which the operator operates the four slave arms by using the two master arms 500*a* and 500*b*. In this case, it is necessary to properly switch the slave arms as operation targets of the master arms. For example, the operator 3 performs such switching by operating the operation unit 600. Obviously, if the number of master arms is equal to that of salve arms to set the operation targets in one-to-one correspondence with the maser arms, there is no need to perform such switching.

The operation unit 600 includes various kinds of operation members such as a switching button for switching slave arms as operation targets of the master arms 500*a* and 500*b* (to be referred to as a switching button hereinafter) and a foot switch for emergently stopping the system. When the operator 3 operates one of the operation members constituting the operation unit 600, the operation unit 600 inputs an operation signal corresponding to the operation of the corresponding operation member to the input processing circuit 700.

The input processing circuit 700 analyzes operation signals from the master arms 500*a* and 500*b* and an operation signal from the operation unit 600 to generate control signals for controlling this surgical system in accordance with the analysis results on the operation signals, and inputs the signals to the slave control circuit 400.

The image processing circuit 800 comprehensively controls the overall surgical system in cooperation with the slave control circuit 400 and the input processing circuit 700. Processing in the flowcharts shown in FIGS. 3 and 5 (to be described later) is performed mainly under the control of the image processing circuit 800.

The image processing circuit 800 generates image data for display on the operator display 900*a* and the assistant display 900*b* by performing various kinds of image processing for the display of image signals input from the slave control circuit 400. The operator display 900*a* and the assistant display 900*b* are formed from, for example, liquid crystal displays, and display images based on the image data generated by the image processing circuit 800 in accordance with the image signals acquired via an observation tool.

In the surgical system having the arrangement shown in FIG. 1 described above, first of all, the sterilized tools 240*a* to 240*d* are attached. This embodiment can use various schemes such as an autoclave sterilization scheme and an EOG sterilization scheme as sterilization processing.

The operator 3 operates the master arms 500*a* and 500*b* while watching the image displayed on the operator display 900*a* based on image signals received via the observation tool attached to the distal end of the slave arm 200*c*. In response to the operations of the master arms 500*a* and 500*b* by the operator 3, the position detectors attached to the links of the master arms 500*a* and 500*b* input detection signals to the input processing circuit 700. When the operator operates the switching button of the operation unit 600, the input processing circuit 700 receives an operation signal from the operation unit 600.

The input processing circuit 700 counts the number of times an operation signal is input from the switching button of the operation unit 600, and switches the slave arms as operation targets of the master arms 500*a* and 500*b* in accordance with the number of times the operation signal is input. In an initial state, for example, the slave arm 200*a* is an operation target of the master arm 500*a*, and the slave arm 200*b* is an operation target of the master arm 500*b*.

In this initial state, when the operator presses the switching button once, the input processing circuit 700 switches the operation target of the master arm 500*a* to the slave arm 200*c* or switches the operation target of the master arm 500*b* to the slave arm 200*d*. Every time the operator presses the switching button once, the input processing circuit 700 switches the operation target of the master arm 500*a* between the slave arm 200*a* and the slave arm 200*c*, or switches the operation target of the master arm 500*b* between the slave arm 200*b* and the slave arm 200*d*.

Upon receiving a detection signal from the position detector of one of the master arms 500*a* and 500*b*, the input processing circuit 700 discriminates the operation amount of the master arm based on the value of the detection signal. The input processing circuit 700 generates a control signal including information indicating the operation amount of the master arm operated by the operator 3 and information for discriminating the slave arm as the operation target of the operated master arm, and inputs the generated control signal to the slave control circuit 400.

The slave control circuit 400 computes a driving amount necessary to make the slave manipulator perform motion corresponding to the operation of the master arm by the operator 3 in accordance with a control signal from the input processing circuit 700. The slave control circuit 400 then controls the magnitude and polarity of a driving signal input to the slave arm as the operation target such that the driving amount of the slave arm as the operation target of the master arm reaches the computed driving amount.

In addition, upon receiving a control signal for emergently stopping the system from the input processing circuit 700 when the operator 3 steps on the foot switch, the slave control circuit 400 stops the slave arms 200*a* to 200*d*.

FIG. 2 is a view showing the second arrangement example of the surgical system according to this embodiment. The case shown in FIG. 2 is premised on a handy-type surgical system. In this case, the handy-type surgical system is the one which makes the operator 3 directly operate the arm to which a surgical tool is attached.

The same reference numerals as in FIG. 1 denote the same or corresponding components in FIG. 2, and hence a description of them will be omitted.

The slave control circuit 400 shown in FIG. 2 is provided to control the operation of the arm 200*c* as a camera arm by the master-slave scheme. If the arm 200*c* is a handy-type arm, the slave control circuit 400 is not required.

Handy arms 200*f* are installed near the operating table 100 like the slave arms 200*a* to 200*d*. Like the slave arms 200*a* to 200*d*, the handy arms 200*f* include a plurality of power units for driving the tools connected to the distal end sides.

The power unit of the handy arm 200*f* generates a power in accordance with a driving signal from an operation unit (not shown) provided for the handy arm 200*f*. As shown in FIG. 2, an adapter 220*f* is connected to the distal end of the handy arm 200*f* in the same manner as shown in FIG. 1, and a tool 240*f* is further connected to the distal end of the adapter 220*f*.

The handy arm 200*f*, the adapter 220*f*, and the tool 240*f* can be respectively replaced with another handy arm 200*g*, another adapter 220*g*, and another tool 240*g*. For example, the assistant 2 performs replacing operation for such tools.

In the surgical system having the arrangement shown in FIG. 2, the operator 3 operates the operation unit (not shown) of the handy arm 200f to drive the handy arm 200f or the tool 240f. Other operations are the same as those described with reference to FIG. 1.

FIG. 3 is a flowchart for a case (abnormal state) in which the image acquired by the imaging system is not properly displayed in the surgical system according to this embodiment.

First of all, when start processing is performed for the surgical system, the image processing circuit 800 reads various kinds of predetermined parameters and flags (step S1), and starts operation (step S2). In this case, the image processing circuit 800 presents the user with the state of a "visual field abnormality flag" of the flags read in step S1 (step S3). This presentation is performed by using, for example, the displays 900a and 900b.

Although described in detail later, the "visual field abnormality flag" is the one that is mainly associated with the occurrence of an abnormal state in the imaging system. In this case, the system is provided with a "monitor abnormality flag", "color abnormality flag", "fogging abnormality flag", "noise abnormality flag", "frame abnormality flag", and "3D one-eye display abnormality flag".

Subsequently, the image processing circuit 800 receives the image data displayed on the displays 900a and 900b from them, and determines, based on the image data, whether the visual field is normal (whether the image acquired from the imaging system is normally displayed) (step S4).

The processing in step S4 (branching from step S4 to step S5 or step S8; the processing in a region D surrounded by the broken line in the flowchart of FIG. 3) will be described in detail below. FIG. 4 is a flowchart showing the details of the processing in step S4 in the flowchart shown in FIG. 3 (branching from step S4 to step S5 or step S8; the processing in the region D surrounded by the broken line in the flowchart of FIG. 3).

As shown in FIG. 4, in this case, the system serially determines a plurality of flags constituting the "visual field abnormality flag" ("monitor abnormality flag", "color abnormality flag", "fogging abnormality flag", "noise abnormality flag", "frame abnormality flag", and "3D one-eye display abnormality flag").

That is, first of all, the image processing circuit 800 determines whether a target monitor (display 900a or 900b) has received video signals (step S4-1). If NO in step S4-1 (the target monitor has received no video signal), the image processing circuit 800 sets the "monitor abnormality flag" to ON (step S8-1).

If YES in step S4-1 or after processing in step S8-1, the image processing circuit 800 determines whether the color balance of the image reproduced and displayed on the target monitor (display 900a or 900b) falls within a normal range (step S4-2). If NO in step S4-2 (the color balance of the reproduced/displayed image does not fall within the normal range), the image processing circuit 800 sets the "color abnormality flag" to ON (step S8-2).

If YES in step S4-2 or after the processing in step S8-2, the image processing circuit 800 determines whether the image reproduced and displayed on the target monitor (display 900a or 900b) is fogged (step S4-3). If YES in step S4-3 (the reproduced/displayed image is fogged), the image processing circuit 800 sets the "fogging abnormality flag" to ON (step S8-3).

If NO in step S4-3 or after the processing in step S8-3, the image processing circuit 800 determines whether the noise of the image reproduced and displayed on the target monitor (display 900a or 900b) falls within a normal range (step S4-4). If NO in step S4-4 (the noise of the reproduced/displayed image does not fall within the normal range), the image processing circuit 800 sets the "noise abnormality flag" to ON (step S8-4).

If YES in step S4-4 or after the processing in step S8-4, the image processing circuit 800 determines whether the image reproduced and displayed on the target monitor (display 900a or 900b) suffers from frame loss (step S4-5). If YES in step S4-5 (the reproduced/displayed image suffers from frame loss), the image processing circuit 800 sets the "frame abnormality flag" to ON (step S8-5).

If NO in step S4-5 or after the processing in step S8-5, the image processing circuit 800 determines whether the image reproduced and displayed on the target monitor (display 900a or 900b) suffers from "one-eye display abnormality in 3d display (whether normal 3D display operation is performed)" (step S4-6). If YES in step S4-6 (the reproduced/displayed image suffers from "one-eye display abnormality in 3d display (normal 3D display operation is not performed)), the image processing circuit 800 sets the "3D one-eye abnormality flag" to ON (step S8-6).

In this case, YES is determined in step S4-6 if, for example, only one of the two endoscopes for acquiring a 3D image cannot acquire a normal stereoscopic image due to contamination on the lens or the like.

Note that when the imaging system of the surgical system is not configured to perform 3D display operation, steps S4-6 and S8-6 are unnecessary steps.

When performing determination in each step (steps S4-1 to S4-6) in the flowchart of FIG. 4 described above, the image processing circuit 800 may determine an abnormality at a given moment in the determination or may determine an abnormality when a given abnormal state continues for a predetermined time (a predetermined ratio).

In the processing example shown in FIG. 4, the image processing circuit 800 serially performs determination on the respective visual field abnormality flags. Obviously, however, it is possible to perform determination concurrently.

If at least one visual field flag is ON after the end of the processing in the flowchart shown in FIG. 4, the process shifts to step S9. If no visual field abnormality flag is set to ON, the process shifts to step S5 (YES in step S4).

If YES in step S4 (the visual field is normal), the image processing circuit 800 sets all the "visual field flags" to OFF, the surgical system is set in the "first mode" (step S6). In this case, the "first mode" is the processing mode to be performed at normal state (when no abnormality has occurred in the imaging system).

Subsequently, the image processing circuit 800 performs display operation by using the displays 900a and 900b to request the user to determine "whether to terminate the surgical system", and determines whether to terminate the surgical system, based on response operation by the user with respect to the display operation (step S7).

If the user performs termination operation for the surgical system, the image processing circuit 800 determines YES in step S7 and writes the visual field abnormality flags set at this time in a nonvolatile memory or the like (step S12), and terminates the surgical system. If NO in step S7, the process shifts to step S3.

If at least one "visual field abnormality flag" is set, the process shifts to step S9.

In step S9, the image processing circuit 800 determines whether the visual field abnormality flags are "valid" (step S9). Step S9 is the one to be executed in consideration of a case in which the visual field abnormality flags have already undergone "invalidation processing" in step S13 (to be described later) and are kept invalid at this time.

If NO in step S9 (the visual field abnormality flags are invalid), the process shifts to step S6. If YES in step S9 (the visual field abnormality flags are valid), the surgical system is set in the "second mode" (step S10).

The following is the detailed processing in step S10. FIG. 5 is a flowchart showing a subroutine for processing (setting to the second mode) in step S10 in the flowchart shown in FIG. 3. First of all, the image processing circuit 800 reads preset "second mode settings" (step S10-1).

The image processing circuit 800 then executes <<abnormality-handling processing>> associated with the visual field abnormality flag (detected <<abnormality detection pattern>>) set to ON at this time, based on the second mode settings read in step S10-1 (step S10-2). Thereafter, the process shifts to step S11 in the flowchart shown in FIG. 3.

The image processing circuit 800 performs display operation by using the displays 900a and 900b to request the user to determine "whether to terminate the surgical system", and determines whether to terminate the surgical system, based on response operation by the user with respect to the display operation (step S11).

If the user performs termination operation for the surgical system, the image processing circuit 800 determines YES in step S11 and writes the visual field abnormality flags set at this time in a nonvolatile memory or the like (step S12), and terminates the surgical system.

If NO in step S11 (the processing in the surgical system is continued), the image processing circuit 800 invalidates the ON states of <<visual field abnormality flags>> set to ON at this time point (step S13).

More specifically, for invalidation processing in step S13, the system may be configured to switch between "valid" and "invalid" by using, for example, a toggle switch or to invalidate the ON state of <<visual field abnormality flag>> for a predetermined time by using a timer function. After the processing in step S13, the process shifts to step S3 described above.

As has been described above, this embodiment can provide a surgical system which includes an imaging system and properly handles a state (abnormal state) in which the image acquired by the imaging system is not normally displayed.

Conventionally, when an abnormality occurs in the imaging system of a surgical system, the operator or the like performs processing, e.g., manually stopping the operation of a slave manipulator, upon recognizing the abnormality in the imaging system. Therefore, it takes some time (time lag) between the occurrence of an abnormality in the imaging system and actual handling of the abnormality. In contrast to this, the surgical system according to this embodiment quickly executes abnormality-handling processing, when an abnormality (e.g., a failure in an endoscope) occurs in the imaging system, regardless of whether the operator recognizes it. This greatly improves the convenience.

In the above case, the system switches between the first and second modes upon ON/OFF setting for the visual field abnormality flags. Obviously, the system may switch the modes as soon as detecting an abnormality.

Although the present invention has been described based on one embodiment, the present invention is not limited to the above embodiment. Obviously, the embodiment can be variously modified and applied within the spirit and scope of the invention.

The above embodiment includes inventions of various stages, and various inventions can be extracted by proper combinations of a plurality of disclosed constituent elements. When, for example, the above problems can be solved and the above effects can be obtained even if several constituent elements are omitted from all the constituent elements in the embodiment, the arrangement from which these constituent elements are omitted can be extracted as an invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical system comprising:
    an image processing circuit configured to determine whether or not an image information acquired by an imaging system corresponds to one of a plurality of abnormality detection patterns associated with one or more abnormalities in the imaging system or one or more abnormalities in a display configured to display the image information; and
    a control circuit configured to switch to and execute an abnormality processing mode in a case where the image processing circuit determines that the image information corresponds to at least one abnormality detection pattern,
        wherein the abnormality processing mode comprises:
            in a case where the image information is determined as corresponding to the plurality of abnormality detection patterns,
                calculating an abnormality-handling processing from the plurality of abnormality detection patterns, and
                executing the calculated abnormality-handling processing; and
            in a case where the image information is determined as corresponding to one abnormality detection pattern, executing a corresponding abnormality processing, and
        wherein calculating the abnormality-handling processing comprises:
            weighting the plurality of abnormality detection patterns, respectively;
            calculating a sum of the weights; and
            identifying the abnormality-handling processing from the sum.

2. A surgical system comprising:
    an image processing circuit configured to determine whether or not an image information acquired by an imaging system corresponds to one of a plurality of abnormality detection patterns associated with one or more abnormalities in the imaging system or one or more abnormalities in a display configured to display the image information; and
    a control circuit configured to switch to and execute an abnormality processing mode in a case where the image processing circuit determines that the image information corresponds to at least one abnormality detection pattern,
        wherein the abnormality processing mode comprises:

in a case where the image information is determined as corresponding to the plurality of abnormality detection patterns,
　　calculating an abnormality-handling processing from the plurality of abnormality detection patterns, and
　　executing the calculated abnormality-handling processing; and
in a case where the image information is determined as corresponding to one abnormality detection pattern, executing a corresponding abnormality processing, and
wherein the abnormality-handling processing comprises withdrawing a slave arm which is provided on the surgical system and has a tool attached to its distal end from a body of a patient.

3. A method comprising:
determining, by an image processing circuit, whether or not an image information acquired by an imaging system corresponds to one of a plurality of abnormality detection patterns associated with one or more abnormalities in the imaging system or one or more abnormalities in a display configured to display the image information; and
switching to and executing, by a control circuit, an abnormality processing mode in a case where the image information is determined as corresponding to at least one abnormality detection pattern,
wherein the abnormality processing mode comprises:
　in a case where the image information is determined as corresponding to the plurality of abnormality detection patterns,
　　calculating an abnormality-handling processing from the plurality of abnormality detection patterns, and
　　executing the calculated abnormality-handling processing; and
　in a case where the image information is determined as corresponding to one abnormality detection pattern, executing a corresponding abnormality processing, and
wherein calculating the abnormality-handling processing comprises:
　weighting the plurality of abnormality detection patterns, respectively;
　calculating a sum of the weights; and
　identifying the abnormality-handling processing from the sum.

4. A method comprising:
determining, by an image processing circuit, whether or not an image information acquired by an imaging system corresponds to one of a plurality of abnormality detection patterns associated with one or more abnormalities in the imaging system or one or more abnormalities in a display configured to display the image information; and
switching to and executing, by a control circuit, an abnormality processing mode in a case where the image information is determined as corresponding to at least one abnormality detection pattern,
wherein the abnormality processing mode comprises:
　in a case where the image information is determined as corresponding to the plurality of abnormality detection patterns,
　　calculating an abnormality-handling processing from the plurality of abnormality detection patterns, and
　　executing the calculated abnormality-handling processing; and
　in a case where the image information is determined as corresponding to one abnormality detection pattern, executing a corresponding abnormality processing,
wherein the abnormality-handling processing comprises withdrawing a slave arm which is provided on a surgical system and has a tool attached to its distal end from a body of a patient.

* * * * *